(12) United States Patent
Piantoni et al.

(10) Patent No.: US 8,439,814 B2
(45) Date of Patent: May 14, 2013

(54) MACHINE AND A METHOD FOR FOLDING NAPPY/DIAPER BLANKS

(75) Inventors: Matteo Piantoni, Albino (IT); Diego Sacchi, Capralba (IT); Marco Rosani, Vailate (IT); Alberto Perego, Milan (IT)

(73) Assignee: GDM S.p.A. (IT)

( * ) Notice: Subject to any disclaimer, the term of this patent is extended or adjusted under 35 U.S.C. 154(b) by 381 days.

(21) Appl. No.: 12/808,544

(22) PCT Filed: Dec. 29, 2008

(86) PCT No.: PCT/IB2008/003641
§ 371 (c)(1),
(2), (4) Date: Jun. 16, 2010

(87) PCT Pub. No.: WO2009/083788
PCT Pub. Date: Jul. 9, 2009

(65) Prior Publication Data
US 2011/0003673 A1    Jan. 6, 2011

(30) Foreign Application Priority Data

Jan. 3, 2008 (IT) .............................. BO2008A0002

(51) Int. Cl.
*B31F 1/10* (2006.01)
(52) U.S. Cl.
USPC ........... 493/416; 493/422; 493/424; 493/435; 493/442; 493/450; 493/454
(58) Field of Classification Search .................. 493/405, 493/416, 418, 422, 424, 425, 432, 434–437, 493/442–444, 450, 454
See application file for complete search history.

(56) References Cited

U.S. PATENT DOCUMENTS 3,689,061 A * 9/1972 Nystrand ...................... 493/369
6,250,357 B1 * 6/2001 Niedermeyer ................ 156/436
(Continued)

FOREIGN PATENT DOCUMENTS

| EP | 1726278 | 11/2006 |
|---|---|---|
| IT | BO2005A000360 | 12/2006 |

OTHER PUBLICATIONS

International Search Report and Written Opinion dated Mar. 18, 2009.

(Continued)

*Primary Examiner* — Christopher Harmon
(74) *Attorney, Agent, or Firm* — Timothy J. Klima; Shuttleworth & Ingersoll, PLC

(57) ABSTRACT

Blanks used in the manufacture of nappies/diapers are folded on a machine comprising a first aspirating roller (5) by which single blanks (2) are advanced in succession toward a second aspirating roller (6) rotating counter and substantially tangential to the first roller (5) at a folding station (T). The first roller (5) is equipped with movable restraining elements (8) designed to engage an intermediate part of each advancing blank (2), so that a leading half of the blank remains free to be taken up by a transfer mechanism (11) operating between the first and second rollers (5, 6) in an area upstream of the folding station (T), and transferred from the first roller (5) to the second roller (6); as the two rollers (5, 6) rotate, the trailing half of the blank (2) retained on the first roller (5) by the restraining elements (8) is drawn closer to the leading half, whereupon the two halves converge gradually until flattened one against the other on passing through the folding station (T), which coincides with the point of tangency between the two rollers (5, 6), and the fold in the blank (2) is complete. The transfer mechanism (11) swings pendulum fashion, moving in sympathy with the first roller (5) when the leading half of the blank (2) is taken up and detached from this roller and in sympathy with the second roller (6) once the leading half of the blank has been released to this same second roller.

16 Claims, 3 Drawing Sheets

U.S. PATENT DOCUMENTS

| | | |
|---|---|---|
| 7,384,386 B2 * | 6/2008 | Sosalla .......................... 493/441 |
| 7,399,266 B2 * | 7/2008 | Aiolfi et al. ................... 493/424 |
| 7,407,161 B2 * | 8/2008 | White ........................... 271/270 |
| 2003/0119641 A1 | 6/2003 | Reising et al. |
| 2003/0226862 A1 | 12/2003 | Vogt et al. |
| 2006/0276320 A1 * | 12/2006 | Aiolfi et al. ................... 493/441 |
| 2008/0176729 A1 * | 7/2008 | Anelli et al. ................... 493/360 |
| 2012/0157284 A1 * | 6/2012 | Coenen et al. ................ 493/405 |
| 2012/0157286 A1 * | 6/2012 | Coenen et al. ................ 493/416 |

OTHER PUBLICATIONS

Russian Office Action dated Mar. 11, 2011 from parallel Russian Patent Application No. 2010126340 (derived form PCT/IB2008/003641 ) filed on Jun. 29, 2010.

* cited by examiner

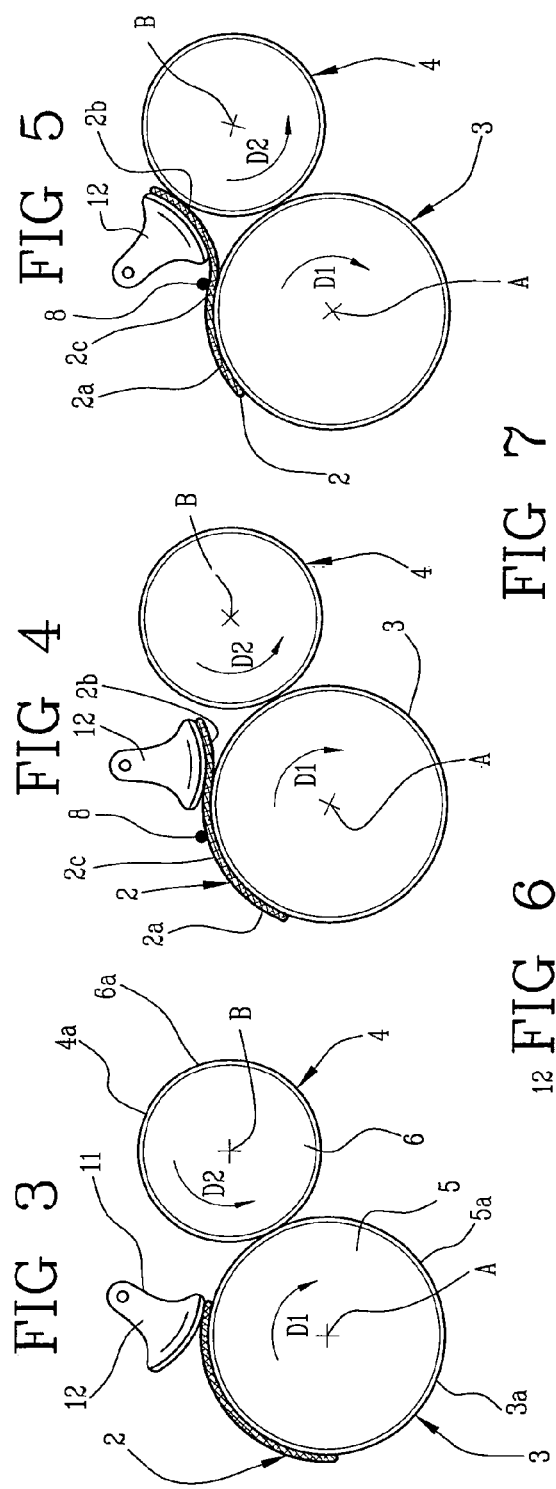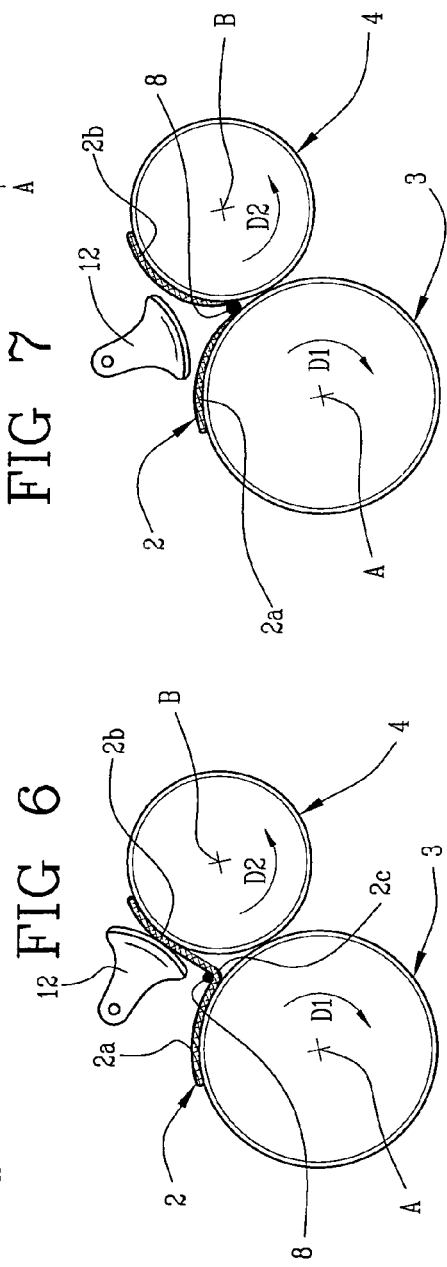

MACHINE AND A METHOD FOR FOLDING NAPPY/DIAPER BLANKS

CROSS-REFERENCE TO RELATED APPLICATIONS

This application is the National Phase of International Application PCT/IB2008/003641 filed Dec. 29, 2008 which designated the U.S. and that International Application was published under PCT Article 21(2) in English.

This application claims priority to Italian Patent Application No. BO2008A000002 filed Jan. 3, 2008, and PCT Application No. PCT/IB2008/003641 filed Dec. 29, 2008, which applications are incorporated by reference herein.

TECHNICAL FIELD

The present invention relates to a machine and to a method for folding blanks used in the manufacture of nappies/diapers.

In particular, and to advantage, the present invention finds application in the manufacture of pant type nappies/diapers.

BACKGROUND ART

A method of the type in question is disclosed in Italian patent application BO2005A000360, incorporated here by reference as if set forth in full, and consists in feeding a succession of flat blanks on a first aspirating wheel or roller, immobilizing a first trailing part or portion of the blank located rearwardmost on the aspirating surface (relative to the direction of rotation of the first wheel), and at the same time causing a second leading part or portion of the blank, located forwardmost relative to the aforementioned direction of rotation, to be distanced gradually from the aspirating surface by means of a second aspirating wheel or roller.

The two rollers rotate continuously about respective axes, with the second revolving substantially tangential to the first.

As the trailing portion of the blank advances on the first aspirating roller, the leading portion of the blank is transferred by the second aspirating roller to a third aspirating outfeed roller, rotating continuously and substantially tangential both to the second roller and to the first roller at a folding or pressing station of the machine.

As the first and third rollers rotate, the two aforementioned portions or halves of the blank are brought together gradually, presenting a V formation in profile, to the point of being folded double on passing through the point of tangential association between the first and third aspirating rollers.

Whilst the method briefly outlined above is extremely simple, it nonetheless betrays one notable drawback, in particular at high production speeds.

Importantly, the first and third rollers turn in opposite directions, rotating convergently and at the same peripheral velocity toward their point of mutual tangency.

Similarly, the first and second rollers turn in opposite directions, rotating convergently and at the same peripheral velocity toward a point of mutual tangency where the leading half of the blank separates from the first roller.

It follows therefore that the second and the third roller must rotate in the same direction, and consequently will be turning counter to one another at their point of mutual tangency.

This creates difficulty in transferring, and particularly, in releasing the forwardmost portion of the blank from the second to the third aspirating roller, even though suction means serving the second roller will be deactivated at the moment of transfer.

Moreover, during the step in which the second portion of the blank is folded flat against the first, one end of the blank remains positioned momentarily between the second roller and the third roller and is subjected to a dragging and pulling force.

Besides affecting the part of the blank located at the point of tangency between the second and third rollers, the force in question can also induce plastic deformations in the entire portion of the blank extending from this same point of tangency to the aforementioned folding station.

In practice, the deformations induced by the dragging and pulling force can often lead to an imperfect match between the second and the first portion of the blank, and this also impacts negatively on subsequent welding or sealing steps that the folded nappy/diaper blanks will undergo.

DISCLOSURE OF THE INVENTION

The object of the present invention is to provide a method and a machine for folding blanks used in the manufacture of nappies/diapers, such as will enable the blanks to be folded easily, and with particular care and precision.

The stated objects are realized in a machine for folding nappy/diaper blanks as recited and characterized in the appended claims.

The stated objects are realized similarly in a method of folding nappy/diaper blanks as recited and characterized in the appended claims.

BRIEF DESCRIPTION OF THE DRAWINGS

The invention will now be described in detail, by way of example, with the aid of the accompanying drawings, in which:

FIGS. 3 ... 7 show a further detail of the machine in FIG. 1, viewed in a series of different operating configurations.

DETAILED DESCRIPTION OF THE PREFERRED EMBODIMENTS OF THE INVENTION

With reference to the accompanying drawings, numeral 1 denotes a machine, in its entirety, for folding and finishing nappies/diapers, in particular pant type nappy/diaper products.

Figure 1:
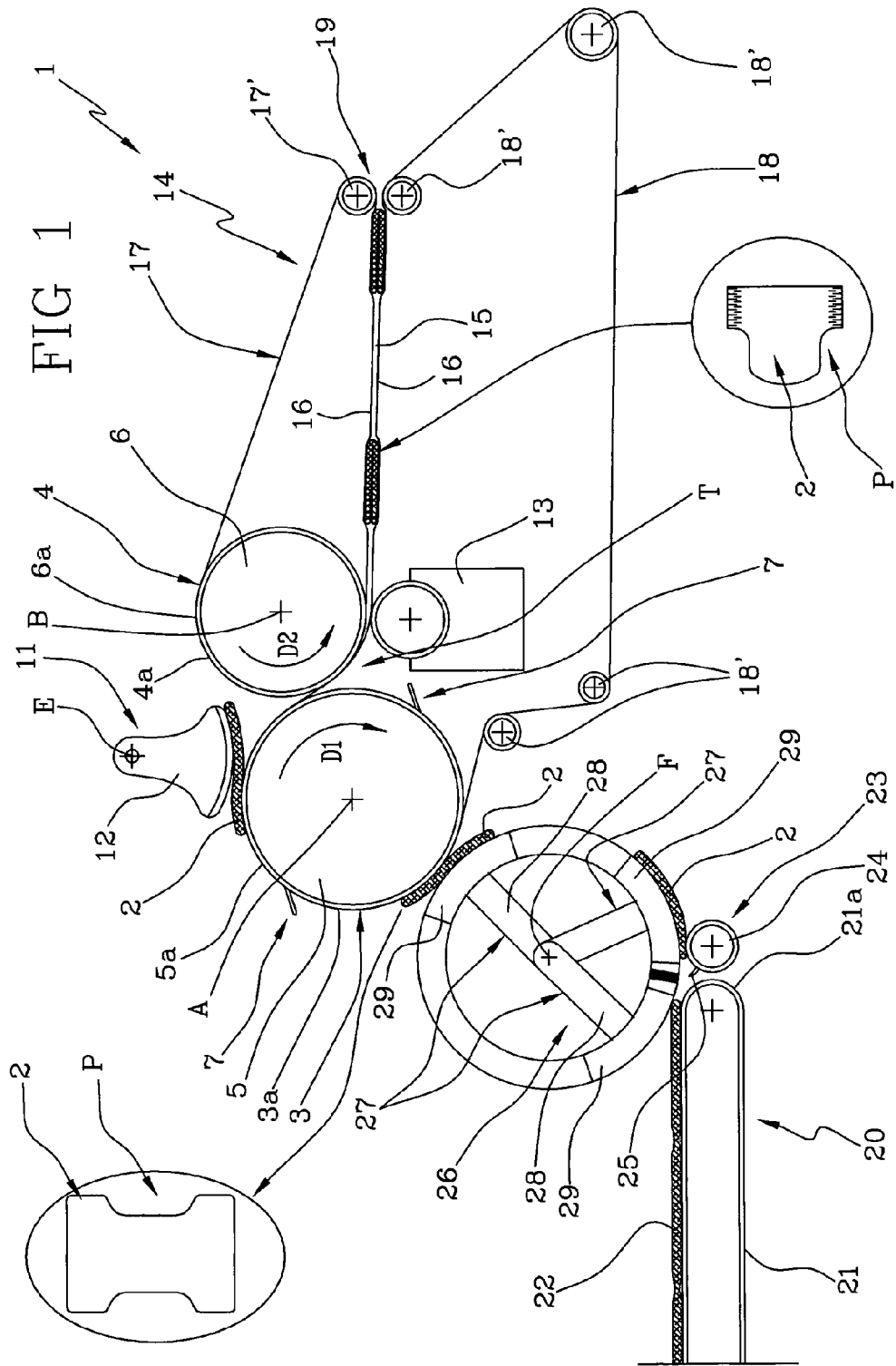
FIG. 1 shows a preferred embodiment of the machine according to the present invention, illustrated schematically and in part.

A pant nappy/diaper of the type to which the present invention relates, denoted P and illustrated schematically in FIG. 1, comprises a closed waistband, which may be elasticated, and attached to the waistband, a padded crotch piece with leg holes.

The single pant P is fashioned from a respective blank 2 presenting a double Tee outline, purely by way of example. More exactly, the blank 2 appears as a longitudinal central band, interconnecting two transverse bands.

The machine 1 comprises a first conveyor 3 by which the blanks 2 are advanced singly and in succession toward a second conveyor 4.

With reference in particular to the preferred embodiment of the drawings, the first conveyor 3 and the second conveyor 4 consist in respective rollers 5 and 6 set in rotation about mutually parallel axes A and B, respectively, and revolving substantially tangential one with another at a position denoted T.

The rollers 5 and 6 rotate at the same angular velocity and in opposite directions, and their tangential speeds at the point of substantial tangency T are identical one with another.

The machine 1 further comprises retaining means 7 associated with the first conveyor 3 and designed to engage each blank 2 by way of an intermediate area, in such a way as to divide the blank 2 for practical purposes into a trailing first portion 2a and a leading second portion 2b, considered relative to the direction of rotation of the roller 5.

As will become clear in the course of the specification, the first portion or half 2a of the blank 2 is retained on the first conveyor 3, whilst the second portion or half 2b is detached from the first conveyor 3 and transferred to the second conveyor 4.

More exactly, the retaining means 7 comprise a plurality of restraining elements 8 equispaced angularly around the cylindrical surface of the roller 5.

Figure 2:
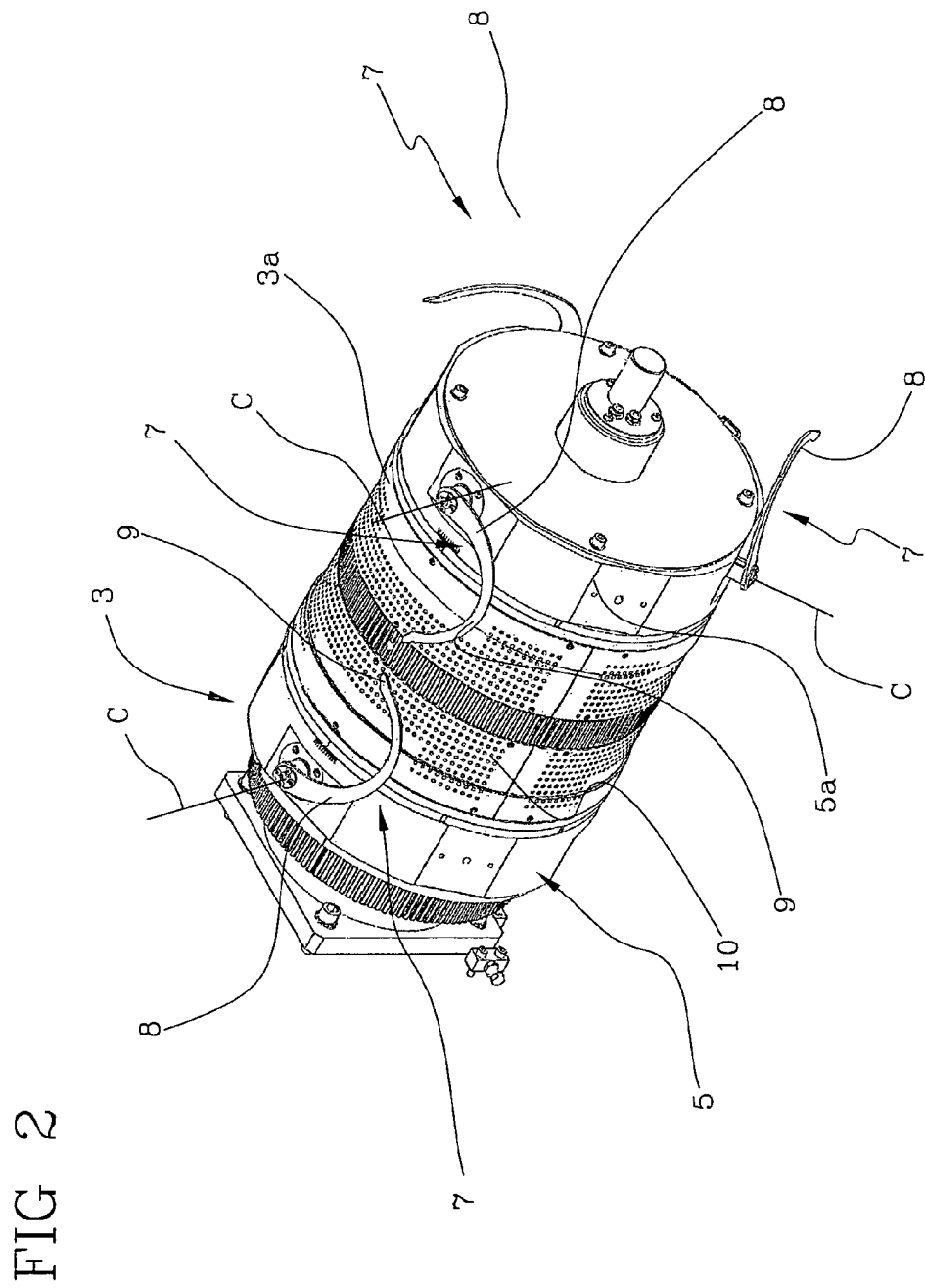
FIG. 2 is a perspective illustration showing a detail of the machine in FIG. 1.

Referring to FIG. 2, each restraining element 8 is composed of two arcuate arms 8a and 8b mounted to the cylindrical outer surface 5a of the roller 5, positioned symmetrically at opposite ends of the selfsame roller 5. Each arm 8a and 8b is mounted pivotably to the roller 5, capable of angular movement about a respective axis C disposed substantially perpendicular to the aforementioned outer surface 5a. The restraining elements 8 are caused to rotate about their respective axes C by suitable motion-inducing means (not illustrated in the drawings).

In particular, the restraining elements 8 are capable of movement between a first position of disengagement from the blank 2, and a second position in which the selfsame elements 8 lie over and in contact with an intermediate area of the blank 2, which as a result is retained at least in part on the first conveyor 3.

In the first position, more exactly, the restraining elements 8 remain completely outside the dimensional envelope of the blank 2.

In the second position, the restraining elements 8 are placed over a central portion 2c of the blank 2 so that this same central portion 2c, at least, is prevented from leaving the first conveyor 3.

The first conveyor 3 and the second conveyor 4 further comprise suction means (connected each to a source of negative pressure, not illustrated) by which the single blanks 2 can be retained on their respective surfaces.

In particular, the suction means operate by creating a partial vacuum through the outer surface 3a of the first conveyor 3 and through the outer surface 4a of the second conveyor 4.

With reference to FIG. 2, the partial vacuum is generated through holes 10 formed in the outer surface 3a of the first conveyor 3. Similarly, the partial vacuum is generated through holes (not illustrated) in the outer surface 4a of the second conveyor 4.

The suction means can be activated selectively according to the position of each successive blank 2 on the first conveyor 3 and/or the second conveyor 4.

The machine 1 further comprises a mechanism 11 located between the first conveyor 3 and the second conveyor 4 and serving to transfer the second portion 2b of the blank 2 from the first to the second conveyor.

The second conveyor 4 combines with the first conveyor 3 to manoeuvre the second portion 2b of the blank 2 into a position folded flat against the first portion 2a retained on the first conveyor 3, as will be made clear in due course.

The transfer mechanism 11 comprises a conveyor 12 in the form of a pendulum, swinging on an axis E parallel to the axes A and B of the rollers 5 and 6 and describing a trajectory tangential to these same rollers between a first limit position of substantially tangential proximity to the one roller 5 and a second limit position of substantially tangential proximity to the other roller 6. In like manner to the rotary conveyors 3 and 4, the pendulum conveyor 12 comprises suction means (not illustrated), which can be activated so as to take up and transfer a single blank 2.

Starting from the first limit position, the pendulum conveyor 12 attracts the second portion 2b of the blank 2 delimited by the restraining elements 8, detaching it from the first conveyor 3, and thereupon swings forward (moving anticlockwise as seen in FIG. 1) to transfer it to the second conveyor 4.

Once in the second limit position, the pendulum conveyor 12 releases the second portion 2b of the blank 2 to the second conveyor 4 and then swings back (in the clockwise direction), moving away from the second conveyor.

The suction means of the pendulum conveyor 12 are activated during the movement from the first limit position to the second, and deactivated during the movement from the second limit position to the first.

Thus, as the pendulum conveyor 12 swings back toward the first conveyor 3, it releases the second portion 2b of the blank 2 to the second conveyor 4 and thereafter has no further interaction with the second portion 2b of the blank 2 in question.

It will be seen from the foregoing that the transfer mechanism 11 swings to and fro, moving in the same direction as the one roller 5 when the second portion 2b of the blank 2 is detached from the revolving surface, and in the same direction as the other roller 6 when the second portion 2b is released to the revolving surface.

As the two rollers 5 and 6 rotate, the trailing half of the blank 2 pinned to the first roller 5 by the retaining means 7 and the leading half of the blank transferred to the roller 6 will assume a V formation, converging gradually until folded flat one against the other on arrival at the aforementioned point of tangency T, which functions as a pressing station, to complete the fold in the blank 2.

The machine 1 comprises a horizontal outfeed channel 15 located downstream of the point T of tangency between the rollers 5 and 6, created between two mutually opposed branches 16 of respective conveyor belts 17 and 18 looped one around the second roller 6 and an idle roller 17', and the other around the first roller 5 and a plurality of idle rollers 18'.

Located at the entry to the outfeed channel 15 is a sealing unit 13 by which the first portion 2a and the second portion 2b of the blank 2 are joined, at least in part, to fashion a nappy/diaper.

The sealing unit 13 is a conventional device such as a heat-sealer or ultrasound welder, and will be located in close proximity to the first conveyor 3 and the second conveyor 4.

The folded and sealed nappies/diapers pass along the channel 15 formed by the two branches 16, toward an outfeed station 19.

The machine 1 further comprises infeed means 20 by which the blanks 2 are supplied to and positioned on the first conveyor 3.

The infeed means 20 comprise a linear conveyor belt 21 carrying a continuous strip 22 of blanks 2 connected one to the next.

Positioned near to one end 21a of the conveyor belt 21 is a cutter device 23 comprising a drum 24, fitted with a knife 25 by which the continuous strip 22 is divided into a succession of separate blanks 2.

The machine 1 also comprises a spacer mechanism 26 operating between the infeed means 20 and the first conveyor 3, serving to feed the cut blanks 2 onto the first conveyor 3 in such a way that one blank 2 will be spaced apart from the next at a distance determined by the rate at which the pendulum conveyor 12 alternates between the two limit positions.

The spacer mechanism 26 comprises a plurality of rotating elements 27 centered on a common axis and rotatable one independently of another in such a way as to take up a cut blank 2 from the infeed means 20 and accelerate it toward the first conveyor 3.

In the example of the drawings, the spacer mechanism 26 comprises three such rotating elements 27 each consisting of an arm 28 pivotable about an axis of rotation, denoted F, and an aspirating carrier element 29.

The present invention relates also to a method of folding blanks 2 used in the manufacture of nappies/diapers.

The method disclosed includes the step of advancing a blank 2 on the first conveyor 3 and retaining a first portion 2a of the blank 2 on this same conveyor.

At the same time, the second portion 2b of the blank 2 is transferred to the second conveyor 4. This second step is affected by the aforementioned transfer mechanism 11.

In accordance with the invention, the method includes a further step of distancing the transfer mechanism 11 from the second portion 2b of the blank 2 immediately after the transfer step has been completed.

Accordingly, there is no interaction between the transfer mechanism 11 and the blank 2 once the blank has been taken up onto the second conveyor 4.

The transfer step and the distancing step are brought about by the pendulum conveyor 12 described and illustrated.

It will be evident from the foregoing description that the transfer step is accomplished by the pendulum conveyor 12 in the course of its movement from the first limit position to the second limit position.

The distancing step, on the other hand, is accomplished by the pendulum conveyor 12 in returning from the second limit position to the first.

With reference in particular to the transfer step, this includes the subsidiary steps of positioning the pendulum conveyor 12 in close proximity to the first conveyor 3 and activating the aforementioned suction means so as to attract the second portion 2b of the blank 2 (FIG. 3).

The pendulum conveyor 12 swings on its axis, passing from the first limit position to the second limit position in such a way that the blank can be offered to the second conveyor 4 (FIGS. 4 and 5). On reaching this position, the suction means are deactivated and the second portion 2b of the blank is able to settle on the second conveyor 4 (FIG. 6).

Once the suction means of the transfer mechanism have been deactivated, the motion of the pendulum conveyor 12 is inverted to initiate the return from the second limit position to the first (FIG. 7). Interference during this step between the pendulum conveyor 12 and the second conveyor 4 is limited advantageously by the arc of travel available to the pendulum conveyor 12.

Likewise during this step, the movement of the pendulum conveyor 12 is contrarotational relative to that of the second conveyor 4, and the angular velocities of the second conveyor 4 and the pendulum conveyor 12 are substantially the same.

The step of transferring the second portion 2b of the blank 2 to the second conveyor 4, once complete, is followed by a step of flattening this same portion against the first portion 2a and thus folding the blank 2 fully in half (FIG. 7) as it reaches a point substantially of mutual tangency between the rollers 5 and 6.

Given that the rollers 5 and 6 are driven in contrarotation, the first and second portions 2a and 2b of the blank 2 can be conveyed toward the point of mutual tangency by conver-gently induced motion. Accordingly, given also the fact that the first portion 2a remains stably associated with the first conveyor 3 during this step, the second portion 2b can be flattened neatly against the first portion 2a of the blank 2 to complete the folding operation.

It will be seen that motion is induced in the blank 2 without pause by the first conveyor 3 and the second conveyor 4. In other words, the movement of the rollers 5 and 6 is continuous.

The method might include the further step of bonding the first portion 2a and the second portion 2b together partially to fashion the nappy/diaper.

Finally, the folded blank 2 is distanced from the rollers and directed along the outfeed channel 15 toward the outfeed station 19.

The stated objects are achieved by the present invention, which affords significant advantages.

In effect, the adoption of the pendulum conveyor 12 ensures that the second portion 2b of the blank 2 can be transferred swiftly and efficiently.

More exactly, as soon as the second portion 2b has been released to the second conveyor 4, the motion of the pendulum conveyor 12 is inverted and assumes the same orientation and peripheral velocity as the motion of the second conveyor 4.

Moreover, the interval of time for which the pendulum conveyor 12 interacts with the second conveyor 4, likewise during the return movement of the selfsame conveyor 12, is noticeably minimized.

Consequently, any dragging and pulling forces exerted on the blank 2 are much reduced, and the risk of damage to the nappy/diaper is advantageously limited.

In addition, this significant reduction of dragging and pulling forces will also reduce the risk of permanent plastic deformation to the blank 2 during the step of folding the first portion 2a and the second portion 2b together.

The blank 2 is therefore folded with precision, even at high production speeds.

The invention claimed is:

1. A machine for folding nappy/diaper blanks, comprising:
    a first conveyor feeding a succession of nappy/diaper blanks toward a second conveyor;
    a retaining mechanism associated with the first conveyor and engageable with an intermediate area of each blank to retain a first portion of the blank on the first conveyor while allowing a second portion of the blank to pass onto the second conveyor;
    a transfer mechanism located between the first conveyor and the second conveyor, by which the second portion of the blank is transferred from the first conveyor to the second conveyor, the second conveyor combining with the first conveyor to manoeuvre at least the second portion of the blank to flatten the second portion against the first portion at a point substantially of mutual tangency between the first conveyor and the second conveyor;
    wherein the transfer mechanism actively engages the second portion of the blank during the transfer from the first conveyor to the second conveyor and is distanced from the second portion once the transfer has been completed;
    wherein the transfer mechanism comprises an alternating pendulum conveyor movable between a first limit position of proximity to the first conveyor and a second limit position of proximity to the second conveyor for transferring the second portion of the blank.

2. The machine as in claim 1, wherein the pendulum conveyor comprises a selectively activated suction mechanism for attracting and transporting the second portion of the blank.

3. The machine as in claim 2, wherein the suction mechanism is are activated during movement from the first limit position to the second limit position to transfer the second portion of the blank from the first conveyor to the second conveyor, and deactivated during movement from the second limit position to the first limit position to release the second portion to the second conveyor.

4. The machine as in claim 1, wherein the pendulum conveyor moves along a trajectory substantially tangential to the first conveyor and the second conveyor.

5. The machine as in claim 1, wherein the first conveyor and the second conveyor comprise respective rollers turning on respective mutually parallel axes.

6. The machine as in claim 5, wherein the first conveyor and the second conveyor further comprise respective suction mechanisms selectively activated according to a position of the blank for retaining and transporting the blank.

7. The machine as in claim 5, wherein the rollers are disposed substantially tangential one to another and driven in contrarotation one relative to another.

8. The machine as in claim 1, wherein the retaining mechanism comprises a plurality of restraining elements arranged uniformly on an outer surface of the first conveyor.

9. The machine as in claim 8, wherein the restraining elements move between a first position of disengagement from the blank, and a second position, placed over the blank to restrain the blank by actively engaging a central portion of the blank.

10. The machine as in claim 4, further comprising an outfeed mechanism by which the folded banks are distanced from the rollers and directed toward an outfeed station.

11. The machine as in claim 10, wherein the outfeed mechanism comprises at least one pair of conveyor belts having respective active branches matched one to another and establishing a channel along which the folded blank is directed.

12. The machine as in claim 1, further comprising a spacer mechanism by which successive blanks are fed to the first conveyor separated by a suitable distance one from a next.

13. A method of folding nappy/diaper blanks, including:
advancing a flat blank on a first conveyor;
retaining a first portion of the blank on the first conveyor;
transferring a second portion of the blank from the first conveyor to a second conveyor with a transfer mechanism;
operating the first conveyor and the second conveyor to fold the second portion of the blank flat against the first portion;
distancing the transfer mechanism from the second portion of the blank immediately after the transferring of the second portion has been completed;
wherein the transferring of the second portion of the blank is brought about by a pendulum conveyor forming part of the transfer mechanism, moving between a first limit position of proximity to the first conveyor and a second limit position of proximity to the second conveyor.

14. The method as in claim 13, wherein the transferring of the second portion of the blank includes placing the pendulum conveyor in the first limit position, activating a suction mechanism associated with the pendulum conveyor, placing the pendulum conveyor in the second limit position, and deactivating the suction mechanism.

15. The method as in claim 13, wherein the distancing of the transfer mechanism from the second portion of the blank includes moving the pendulum conveyor from the second limit position to the first limit position.

16. The method as in claim 13, wherein a feed motion of the blank induced by the first conveyor and the second conveyor is continuous.

* * * * *